(12) United States Patent
Nason et al.

(10) Patent No.: US 11,844,510 B2
(45) Date of Patent: Dec. 19, 2023

(54) ALL-SUTURE SUTURE ANCHOR SYSTEMS AND METHODS

(71) Applicant: CAYENNE MEDICAL, INC., Scottsdale, AZ (US)

(72) Inventors: Kevin S. Nason, Chandler, AZ (US); Hoang P Nguyen, Goodyear, AZ (US); Kevin N. Baird, Scottsdale, AZ (US); Derek J. Harper, Scottsdale, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 458 days.

(21) Appl. No.: 17/195,054

(22) Filed: Mar. 8, 2021

(65) Prior Publication Data
US 2021/0186484 A1  Jun. 24, 2021

Related U.S. Application Data

(63) Continuation of application No. 15/434,642, filed on Feb. 16, 2017, now Pat. No. 10,966,703, which is a
(Continued)

(51) Int. Cl.
*A61B 17/04* (2006.01)
*A61B 17/17* (2006.01)
(Continued)

(52) U.S. Cl.
CPC ...... *A61B 17/0401* (2013.01); *A61B 17/0482* (2013.01); *A61B 17/0483* (2013.01);
(Continued)

(58) Field of Classification Search
CPC ............ A61B 17/0401; A61B 17/0482; A61B 17/0483; A61B 17/0487; A61B 17/1796;
(Continued)

(56) References Cited

U.S. PATENT DOCUMENTS

4,450,782 A * 5/1984 Tortell ................... D05C 17/00
                                                                112/439
5,133,723 A    7/1992 Li
(Continued)

FOREIGN PATENT DOCUMENTS

WO   WO-2013003746 A1   1/2013
WO   WO-2015134800 A1   9/2015

OTHER PUBLICATIONS

U.S. Appl. No. 14/639,943 U.S. Pat. No. 9,622,740, filed Mar. 5, 2015, All-Suture Suture Anchor Systems and Methods.
(Continued)

*Primary Examiner* — Diane D Yabut
*Assistant Examiner* — Rachel S Highland
(74) *Attorney, Agent, or Firm* — SCHWEGMAN LUNDBERG & WOESSNER, P.A.

(57) ABSTRACT

A method of anchoring soft tissue to a suitable bone site, using a soft suture anchor, includes steps of disposing the soft suture anchor on a shaft of an inserter, and securing a proximal end of a tensioning suture limb, extending proximally from the soft suture anchor, to structure in a handle of the inserter, so that it is maintained in place at a first level of holding tension ($T_{hold}$). The inserter shaft is inserted into a hone hole at a desired procedural site, so that the soft suture anchor is positioned at a location where it is to be anchored. A further step involves actuating a control mechanism in the inserter handle to move the structure proximally to apply a second level of deployment tension ($T_{load}$) to the tensioning suture limb.

18 Claims, 9 Drawing Sheets

Related U.S. Application Data continuation of application No. 14/639,943, filed on Mar. 5, 2015, now Pat. No. 9,622,740.

(60) Provisional application No. 61/948,543, filed on Mar. 5, 2014, provisional application No. 62/094,866, filed on Dec. 19, 2014.

(51) Int. Cl.
*A61B 17/00* (2006.01)
*A61B 90/00* (2016.01)
*A61F 2/08* (2006.01)

(52) U.S. Cl.
CPC ...... *A61B 17/0487* (2013.01); *A61B 17/1796* (2013.01); *A61B 17/0467* (2013.01); *A61B 90/03* (2016.02); *A61B 2017/00526* (2013.01); *A61B 2017/0406* (2013.01); *A61B 2017/0409* (2013.01); *A61B 2017/049* (2013.01); *A61B 2017/0411* (2013.01); *A61B 2017/0474* (2013.01); *A61B 2017/0477* (2013.01); *A61B 2017/0488* (2013.01); *A61B 2017/0496* (2013.01); *A61F 2002/0882* (2013.01)

(58) Field of Classification Search
CPC ................ A61B 17/0467; A61B 90/03; A61B 2017/00526; A61B 2017/0406; A61B 2017/0409; A61B 2017/0411; A61B 2017/0474; A61B 2017/0477; A61B 2017/0488; A61B 2017/049; A61B 2017/0496; A61B 17/0485; A61B 2017/0475; A61B 17/06166; A61F 2002/0882; A61F 2002/0817; A01K 91/047

See application file for complete search history.

(56) References Cited

U.S. PATENT DOCUMENTS

| | | | | |
|---|---|---|---|---|
| 5,217,470 | A * | 6/1993 | Weston | A61B 17/0469 606/1 |
| 5,578,057 | A | 11/1996 | Wenstrom, Jr. | |
| 5,628,756 | A * | 5/1997 | Barker, Jr. | A61F 2/08 606/228 |
| 6,102,934 | A | 8/2000 | Li | |
| 6,171,317 | B1 * | 1/2001 | Jackson | A61B 17/0469 289/17 |
| 7,731,732 | B2 * | 6/2010 | Ken | A61B 17/0057 606/213 |
| 8,403,947 | B2 * | 3/2013 | Ochiai | A61F 2/0811 606/144 |
| 9,445,803 | B2 * | 9/2016 | Marchand | A61B 17/0401 |
| 9,622,740 | B2 | 4/2017 | Nason et al. | |
| 2006/0271060 | A1 | 11/2006 | Gordon | |
| 2007/0203508 | A1 * | 8/2007 | White | A61B 17/0401 606/148 |
| 2008/0009904 | A1 | 1/2008 | Bourque et al. | |
| 2008/0275477 | A1 | 11/2008 | Sterrett et al. | |
| 2009/0312794 | A1 | 12/2009 | Nason et al. | |
| 2009/0326562 | A1 | 12/2009 | White et al. | |
| 2010/0087837 | A1 | 4/2010 | Jaramillo et al. | |
| 2010/0179573 | A1 | 7/2010 | Levinsohn et al. | |
| 2011/0022083 | A1 * | 1/2011 | DiMatteo | A61B 17/06166 606/228 |
| 2011/0028997 | A1 | 2/2011 | Gregoire et al. | |
| 2011/0098727 | A1 | 4/2011 | Kaiser et al. | |
| 2011/0172682 | A1 | 7/2011 | Brady et al. | |
| 2011/0208239 | A1 * | 8/2011 | Stone | A61B 17/06004 606/228 |
| 2011/0218538 | A1 | 9/2011 | Sherman et al. | |
| 2011/0264141 | A1 * | 10/2011 | Denham | A61B 17/0401 606/232 |
| 2012/0053622 | A1 | 3/2012 | Schulman | |
| 2012/0143215 | A1 | 6/2012 | Corrao et al. | |
| 2012/0158044 | A1 | 6/2012 | Jenson et al. | |
| 2012/0239085 | A1 | 9/2012 | Schlotterback et al. | |
| 2013/0079822 | A1 * | 3/2013 | Maiorino | A61B 17/06166 606/232 |
| 2013/0110165 | A1 | 5/2013 | Burkhart et al. | |
| 2013/0123810 | A1 | 5/2013 | Brown et al. | |
| 2013/0296934 | A1 * | 11/2013 | Sengun | A61B 17/0401 606/232 |
| 2015/0250471 | A1 | 9/2015 | Nason et al. | |
| 2017/0156718 | A1 | 6/2017 | Nason et al. | |

OTHER PUBLICATIONS

U.S. Appl. No. 15/434,642, filed Feb. 16, 2017, All-Suture Suture Anchor Systems and Methods.
"U.S. Appl. No. 14/639,943, Non Final Office Action dated May 20, 2016", 9 pgs.
"U.S. Appl. No. 14/639,943, Notice of Allowance dated Dec. 12, 2016", 9 pgs.
"U.S. Appl. No. 14/639,943, Preliminary Amendment filed Feb. 19, 2016", 6 pgs.
"U.S. Appl. No. 15/434,642, Advisory Action dated Feb. 18, 2020", 4 pgs.
"U.S. Appl. No. 15/434,642, Final Office Action dated Nov. 29, 2019", 15 pgs.
"U.S. Appl. No. 15/434,642, Non Final Office Action dated May 16, 2019", 15 pgs.
"U.S. Appl. No. 15/434,642, Non Final Office Action dated Aug. 18, 2020", 17 pgs.
"U.S. Appl. No. 15/434,642, Notice of Allowance dated Dec. 8, 2020", 9 pgs.
"U.S. Appl. No. 15/434,642, Preliminary Amendment filed Feb. 17, 2017", 6 pgs.
"U.S. Appl. No. 15/434,642, Response filed Jan. 24, 2020 to Final Office Action dated Nov. 29, 2019", 10 pgs.
"U.S. Appl. No. 15/434,642, Response filed Aug. 15, 2019 to Non Final Office Action dated May 16, 2019", 10 pgs.
"U.S. Appl. No. 15/434,642, Response filed Nov. 18, 2020 to Non Final Office Action dated Aug. 18, 2020", 11 pgs.
"Application Serial No. 15759042.3 Response filed Apr. 7, 2017 to office action dated Oct. 12, 2017.", 20 pgs.
"European Application Serial No. 15759042.3, Communication Pursuant to Article 94(3) EPC dated Feb. 6, 2020", 4 pgs.
"European Application Serial No. 15759042.3, Extended European Search Report dated Oct. 12, 2017", 8 pgs.
"European Application Serial No. 15759042.3, Response filed Apr. 23, 2018 to Extended European Search Report dated Oct. 12, 2017", 11 pgs.
"European Application Serial No. 15759042.3, Response filed Jun. 16, 2020 to Communication Pursuant to Article 94(3) EPC dated Feb. 6, 2020", 9 pgs.
"International Application Serial No. PCT/US2015/019047, International Search Report (dated Jun. 12, 2015", 6 pgs.
"International Application Serial No. PCT/US2015/019047, Written Opinion dated Jun. 12, 2015", 7 pgs.

* cited by examiner

ALL-SUTURE SUTURE ANCHOR SYSTEMS AND METHODS

This application claims the benefit under 35 U.S.C. 119(e) of the filing date of Provisional U.S. Application Ser. No. 61/948,543, entitled All-Suture Anchor with Inserter, filed on Mar. 5, 2014, and of the filing date of Provisional U.S. Application Ser. No. 62/094,866, entitled All-Suture Anchor with Inserter, filed on Dec. 19, 2014. Both of these prior applications are herein expressly incorporated herein by reference, in their entirety.

BACKGROUND OF THE INVENTION

There are many soft-tissue to bone repair procedures, such as rotator cuff SLAP and Bankart lesion repairs, or reconstruction of labral tissue to the glenoid rim, in which a surgeon needs to secure tissue in close contact with bone by implanting an anchor, pre-loaded with suture, into a hole drilled in the bone at the desired anchor location. Commonly, the anchor which the sutures are attached to is made of either plastic such as PEEK or metal such as Titanium or Stainless Steel. Such anchors function like a nail or screw to secure them into the bone. Floating sutures, loaded into the rigid anchor body, are then passed through soft tissue near the anchor and the soft tissue is compressed against the bone surface by tying the suture ends into a knot. When the soft tissue is directly compressed against a bony surface, the body's healing response will affix the soft tissue to the bone to complete the repair. In the case of an implant pulling out of the bone there is a piece of hard material from that implant floating inside the joint space. That piece of material could temporary or permanently be stuck within the joint, causing damage to the articulating surfaces.

Many surgeons are beginning to favor using ail-suture suture anchors over traditional suture anchors. One particular advantage of using an all-suture anchor is that it requires a smaller hole to be drilled to the bone. Preserving bone is preferred by surgeons. There are quite a few all-suture anchor designs on the market today intended to capture this trend.

The JuggerKnot™, by Biomet, has its anchor configuration made of a section of #5-polyester suture. The loaded suture is inserted through the length of the #5 suture section of the anchor. The anchor is preloaded on an inserter at the middle point. The inserter pushes the anchor into a drilled hole in the bone until a desired position is reached. The inserter is then removed. Both suture limbs are lightly pulled to contract the anchor, expanding it laterally against the wall of the drilled hole. This design relies on the friction between the suture ball of the anchor and the bone. Depending upon the position inside the hole to which the anchor is deployed or set, anchor slippage may occur when higher tension applied on tire anchor until the anchor may move to a harder bone surface such as the cortex.

ConMed Linvatec also has introduced an anchor called the Y-Knot™. The anchor is very much the same construct as the Biomet JuggerKnot anchor in terms of design, but with different suture material. It uses high-strength suture for the anchor instead of polyester suture. The technique for using the anchor is also very similar as the company suggests in its own words: "Drill Pilot Hole. Insert Anchor, and Pull-to set." Since the anchor designs and techniques are similar-, the anchor shares the same weakness of relying on friction. Thus, slippage can occur, and pull out strength could not be adequate.

Another similar anchor is from Stryker and is called Iconix™. The anchor is designed to have opening sections along the sheet portion, which claim to provide a bunching effect using targeted compression zones. The middle point of the anchor is also preloaded on an inserter and inserted into a pre-drilled hole. When deployed by applying tension on the pre-loaded suture limbs, instead of the whole section of the anchor expanding randomly within the hole, those opening sections on the anchor are intended to swing outward laterally up to 3 mm-4 mm. However, such claimed expansion dimensions are theoretical only, because the soft suture is not stiff enough to penetrate the hole to achieve such dimensions in practice.

All of the foregoing anchors are offered in different sizes (defined by the size of the hole drilled into the bone) and are pre-loaded with different sizes and numbers of floating sutures. All of these anchors, as noted above, are similar in construction: a floating suture or sutures are passed through a tube of larger suture. There may be one or more windows cut in the tube to allow the construct to bend at certain locations, as well as to allow the floating sutures to pass between the inside and outside of the tube. All of the anchors are then loaded onto similar inserters meant to push the anchor into a tunnel drilled into the bone. The anchors are wrapped around the top of the inserter shaft and secured in a fork at the tip. The floating sutures are routed along the inserter shaft and are secured in a cleat in the inserter handle.

Advantages of all-suture anchors that have resulted in their increased popularity in orthopedic procedures include:

a) the need for a smaller bone tunnel, because all-suture anchors deploy and change shape inside the bone tunnel, meaning that the drilled hole can be smaller than for rigid anchors with similar strength. This results in less bone removal and the ability to place anchors closer together when necessary;

b) ease of revision, because if an all-suture anchor does not deploy correctly, or if the surgeon is not comfortable with the bone quality after drilling the bone tunnel, the small hole allows the practitioner to drill a slightly larger hole in the same location and to use a traditional rigid anchor. If the anchor is deployed, it is easy for the surgeon to drill through or remove the anchor in order to implant another one; and c) patient safety. In some cases, anchors can back out or be pulled out of the bone by patient activity or re-injury. If the anchor is located in a joint space, such as in the glenoid, and it pulls out of the bone after surgery, the soft material will, not damage the bone surfaces (such as the humeral head) as can be the case with a rigid anchor.

All of the foregoing anchors are also deployed in similar manners. Once the anchor is placed at the bottom of the bone tunnel, the floating sutures are removed from the inserter handle and the inserter is removed. To deploy the anchor, the physician is required to pull on the floating sutures. This tension applied to the floating sutures pulls the anchor upwardly in the bone tunnel, and the friction between the anchor and the bone causes the anchor to change shape and expand to create an interference fit in the tunnel. In addition, the larger diameter of the anchor prevents it from pulling up through the smaller hole in the harder cortical bone near the surface. The floating sutures are then passed through soft tissue and the remaining procedural steps are identical to those of any other pre-loaded suture anchor.

Currently available all-suture anchors require manual tensioning by the practitioner in order to deploy the anchor, as noted above. Often, to avoid anchor pullout in soft bone, the practitioner will pull gently on one suture limb, then pull on the other, and back and forth in like manner until the anchor is deployed. The amount of tension required to fully deploy the anchor depends upon the bone quality, as well as practitioner skill, training, and experience. At a minimum, this results in inconsistent tension applied to deploy the anchor. This, in turn, will lead to inconsistent performance, both in cyclic displacement and ultimate pull-out strength. If the practitioner is concerned about the bone quality and only pulls gently to deploy the anchor (to avoid pulling the anchor out), fee anchor displacement under cyclic loading will be greater and the ultimate pullout force could be reduced. Another failure mode is the anchor not expanding properly and pulling out of the bone tunnel during practitioner tensioning. This can happen if fee bone is very hard and the anchor cannot properly expand, or if the bone is very soft and the practitioner pulls hard enough to overcome fee maximum pullout force of the anchor.

SUMMARY OF THE INVENTION

The present invention comprises an all-suture anchor together with an inserter and drill guide to deploy the anchor in bone. The inserter is designed to pull a specific and consistent range of tension each time in order to deploy the anchor in a bone tunnel. The drill guide provides a large footprint at the surface of the bone around the drill hole to protect the bone during anchor deployment.

The amount of force applied to deploy the anchor is very important to its post-operative performance. For example, if the anchor is deployed by pulling at a particular level of tension on the sutures (40 N in one particular example), it will expand and move to a certain position in the bone tunnel. The sutures are then passed through soft tissue, and tied down to secure the tissue against, the bone. During post-operative activity and rehabilitation by the patient (prior to tissue healing), forces are exerted on the soft tissue and transferred through the suture to tire anchor, if these forces are below the deployment tension level (40 N in our example), the anchor will remain in the same position. However, if the anchor is exposed to loads higher than the deployment force, it is likely to be pulled toward the surface of the bone. This movement can cause slack in the suture and allow a gap to form between the tissue and the bone, resulting in a failed repair. If the anchor is deployed at 100 N during surgery, for example, it will remain stable at loads below this value. If it is pulled with too much force during deployment (more than its maximum pull-out force in that bone), it may pull out, especially if the bone Is very soft or very hard.

Bench testing, cadaver testing, and the literature review have been used to determine the appropriate minimum load foe anchor should withstand post-operatively. Several cyclic loading studies by Barber et al. Specify cyclic loading from 0 to 60 N to simulate forces applied to the suture anchors post-operatively, prior to tissue healing. Mazzocca et al. Deemed a peak cyclic load of 100 N (for a 3-anchor construct sharing the load) to be appropriate for rotator cuff testing. The present invention is designed to deploy the anchor with a minimum, preferably, of approximately 60 N of tension so that the anchor will not move when exposed to this load post-operatively. This Is more tension that a physician can easily apply by hand, especially with only one floating suture loaded in the anchor.

Bench and cadaver testing were performed to determine the upper range of the tension with, which to deploy the anchor. Applying too much tension can cause the anchor to pull out of the bone, especially in very soft or very hard bone. In very soft bone, excessive tension can cause the deployed anchor to pull upwardly through the soft bone. In very hard bone, the anchor cannot displace bone to fully expand to a larger diameter inside the tunnel. If it is deployed with more tension that the compression fit can withstand, the anchor will slide out of the hole. One particular embodiment of the present, invention was tested in a range of bone block densities that simulate a range from very soft to very hard bone, as well as human cadaver bones. An upper limit of approximately 150 N was found to be appropriate for proper deployment across the range of hone densities.

The inventive inserter utilizes a knob to turn a screw to apply tension to the floating sutures. This design provides a mechanical advantage and allows the inserter to pull more tension to deploy the anchor than a surgeon can reliably pull by hand to achieve the desired range of deployment tension (60-150 N).

Another important component of the present inventive system is the drill guide. Most, suture anchors on the market utilize a drill guide to help locate and maintain the position of the drill on the bone surface as well as to guide the anchor into the hole at the same angle as the drilled hole. For the described all-suture anchor of the present invention, the drill guide plays an integral role and is designed to aid in the anchor deployment. Since the inserter pulls on the anchor with a significant amount of tension, the opposing reaction force pulls the inserter against the bone surface. If the anchor were deployed without a drill guide, in soft, bone, the deployment forces would pull the anchor upwardly toward the surface of the bone and simultaneously pull the inserter shaft downwardly into the bone, and full tension would not be reached. Most drill guides are made from thin-walled tubing to keep the outer diameter as small as possible. However, this thin, knife-kike edge at the tip can create a cylindrical cut into the bone around the tunnel if forced into the bone. This can also happen if the practitioner mallets too hard on the inserter handle. If the inserter handle bottoms out on the drill guide, subsequent malleting will drive the inserter and drill guide into bone and damage tire surface. The drill guide used with the described anchor and inserter has a much thicker wall section at the tip that provides a larger surface area to resist the downward forces (applied by the inserter during anchor deployment or by the practitioner during malleting). This downward pressure from the drill guide tip also protects the bone from damage or breaking as the anchor is pulled upwardly during deployment. If the anchor is manually deployed and the practitioner pulls very hard to deploy the anchor, it will expand and the force is then transmitted to the bone above it. If tire hone is weak, it could break and leave a large crater on the surface of the bone. In the inventive system, the drill guide helps to prevent this mode of failure.

Another improvement relates to the construction of the anchor itself. Many anchor designs were built and tested to determine the construction that could be inserted into the smallest diameter and shortest hole depth, and at the same time expand consistently to have the lowest cyclic displacement and highest pull-out force.

More particularly, in one aspect of the invention, there is disclosed a soft suture anchoring system which comprises a suture anchor fabricated entirely of soft material, comprising a length of suture having a plurality of loops disposed therein and further comprising a tensioning suture limb disposed along the suture anchor and extending from one end of the suture anchor. An inserter is also provided for inserting the suture anchor into a bone hole, wherein the inserter comprises a shaft for holding and deploying the suture-anchor and a handle proximal to the shaft. The handle comprises a structure attachable to the tensioning suture limb for holding and maintaining the tensioning limb under a first level of holding tension ($T_{hold}$) sufficient to hold the tensioning suture limb in place, and a tensioning mechanism which moves the structure proximally to apply a second level of deployment tension ($T_{load}$) to the tensioning limb to expand a lateral dimension of the suture anchor in order to deploy the anchor.

In one disclosed embodiment of the invention, the structure comprises a crossbar. The crossbar is connected to the shaft, so that the crossbar moves axially when the shaft moves axially. The tensioning mechanism comprises a knob connected to a proximal end of the shaft, wherein rotation of the knob causes the shaft to move axially in a proximal direction. Specifically, in one approach, the proximal end of the shaft comprises external threads and the knob comprises internal threads which are engaged with the external threads, wherein rotation, of the knob causes the shaft to be rotatably retracted proximally into the knob because of the threaded engagement of the knob and the shaft.

A pinching mechanism is provided for pinching the tensioning suture limb against the crossbar. In one embodiment of the invention, the pinching mechanism comprises a pinching pin disposed adjacent to the crossbar. The pinching pin may be positionally fixed, or it may be axially movable to adjust $T_{hold}$ and $T_{load}$ to a desired level. In illustrated embodiments of the invention, $T_{load}$ is 60 N-150 N. However, in certain cases, using the axially movable pinching pin, the desired level of $T_{hold}$ and $T_{load}$ is lower than 60 N.

In the disclosed invention embodiments, the shaft comprises an inner shaft, and the inserter further comprises an outer shaft surrounding the inner shaft.

In another aspect of the invention, there is disclosed an inserter system for a soft suture anchoring system, wherein the inserter includes a shaft for holding and deploying a soft suture anchor and a handle proximal to the shaft. The handle comprises a structure attachable to the tensioning suture limb for holding and maintaining the tensioning limb under a first level of holding tension ($T_{hold}$) sufficient to hold the tensioning suture limb in place, and a tensioning mechanism which moves the structure proximally to apply a second level of deployment tension ($T_{load}$) to the tensioning limb to expand a lateral dimension of the suture anchor in order to deploy the anchor.

In one disclosed embodiment of the invention, the structure comprises a crossbar. The crossbar is connected to the shaft, so that the crossbar moves axially when the shaft moves axially. The tensioning mechanism comprises a knob connected to a proximal end of the shaft, wherein rotation of the knob causes the shaft to move axially in a proximal direction. Specifically, in one approach, the proximal end of the shaft comprises external threads and the knob comprises internal threads which axe engaged with the external threads, wherein rotation of the knob causes the shaft to be rotatably retracted proximally into the knob because of the threaded engagement of the knob and the shaft.

A pinching mechanism is provided for pinching the tensioning suture limb against the crossbar. In one embodiment of the invention, the pinching mechanism comprises a pinching pin disposed adjacent to the crossbar. The pinching pin may be positionally fixed, or it may be axially movable to adjust $T_{hold}$ and $T_{load}$ to a desired level. In illustrated embodiments of the invention, $T_{load}$ is 60 N-150 N. However, in certain cases, using the axially movable pinching pin, the desired level of $T_{hold}$ and $T_{load}$ is lower than 60 N.

In the disclosed invention embodiments, the shaft comprises an inner shaft, and the inserter further comprises an outer shaft surrounding the inner shaft.

In yet another aspect of the invention, there is disclosed a method of anchoring soft tissue to a suitable bone site, using a soft suture anchor. The method comprises steps of disposing the soft suture anchor on a shaft of an inserter, and securing a proximal end of a tensioning suture limb extending proximally from the soft suture anchor to structure in a handle of the inserter, so that it is maintained in place at a first level of holding tension ($T_{hold}$). The inserter shaft is inserted into a bone hole at a desired procedural site, so that the soft suture anchor is positioned at a location where it is to be anchored. A further step involves actuating a control mechanism in the inserter handle to move the structure proximally to apply a second level of deployment tension ($T_{load}$) to the tensioning suture limb.

The invention, together with additional features and advantages thereof, may best be understood by reference to the following description taken in conjunction with the accompanying illustrative drawing.

DETAILED DESCRIPTION OF THE INVENTION

Figure 1:
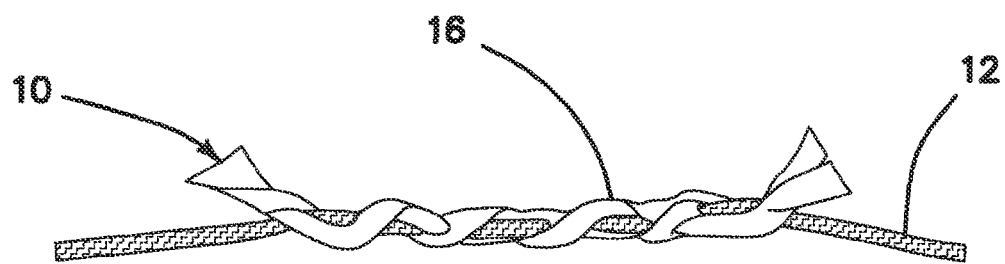
FIGS. 1-9 are views illustrating the construction of a suture anchor according to a first embodiment, of the invention.

Referring now more particularly to the drawings, there is shown in FIG. 1 a suture anchor 10 comprised entirely of a suture material, as well as a floating suture 12. It should be noted, at this juncture, that the invention comprises an inserter that applies tension to the floating sutures of an all-suture anchor in order to expand it within the hone tunnel to produce an interference fit of the anchor with the walls of the bone tunnel. The construction of the anchor itself also helps to provide a strong and secure anchor point, in the bone. There are two particularly preferred methods of constructing the anchor 10 that result in a large change between the aspect ratio of the non-deployed anchor and the deployed anchor. It is desirable for the anchor 10 to be short and think for the insertion step of the procedure so that it can fit into a shallow, small diameter hole. This results in the least volume of bone removed from the patient. During deployment, the anchor 10 should expand as much as possible to provide compression against the walls of the bone tunnel, and to prevent it from pulling through the small diameter hole in the cortical bone at the tunnel entrance.

Figure 2:
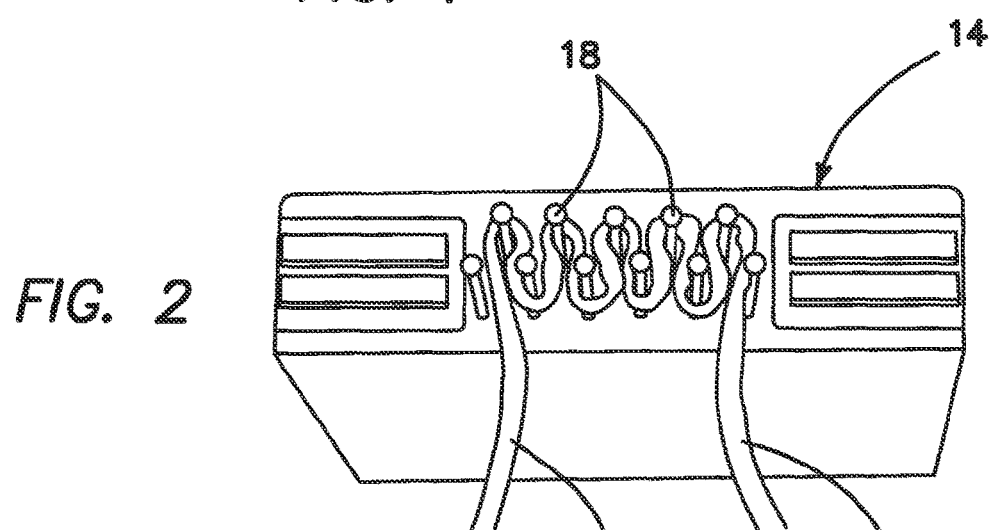
Figure 3:
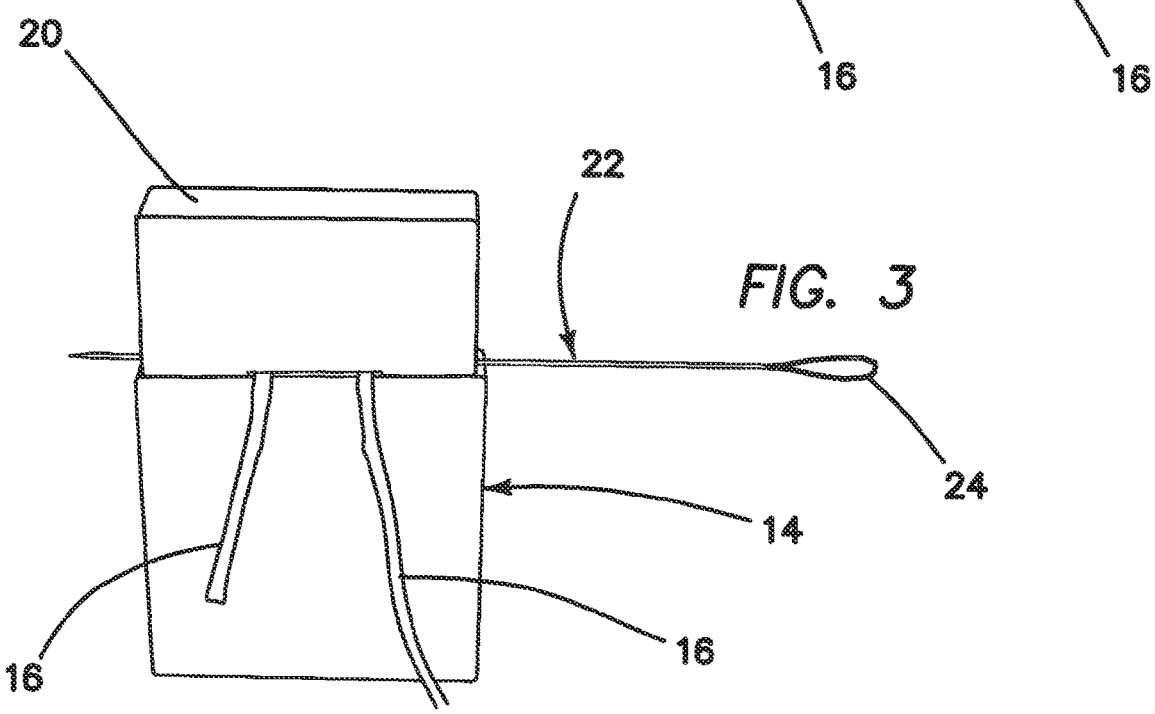
Figure 4:
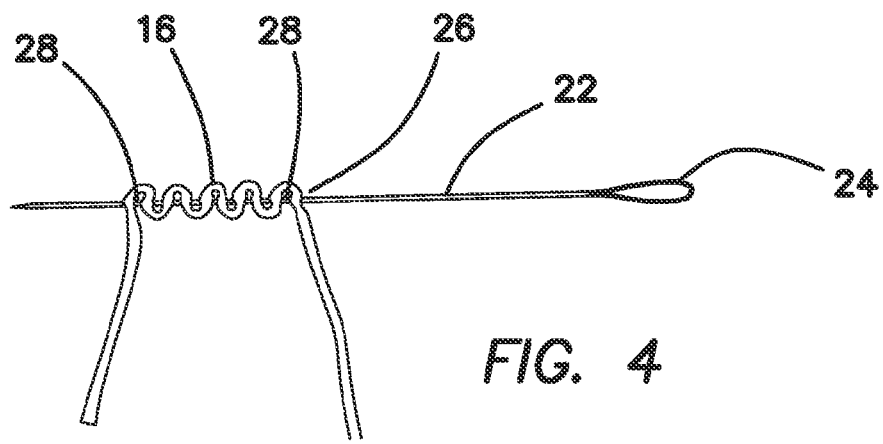

Thus, FIG. 1 illustrates a first, embodiment of a suture anchor 10 constructed in accordance with the principles of the present, invention. This embodiment is a single-loaded anchor. FIG. 2 illustrates an assembly fixture 14, wherein a piece of size 2 suture 16 (anchor suture) is wrapped around pins 18 of the fixture 14, as shown. As shown in FIG. 3, a cap 20 is placed on the fixture 14 and a needle 22 with a snare loop 24 on one end is pierced through the anchor suture 16. Then, the assembly 26 is removed from the fixture, as shown in FIG. 4.

Figure 5:
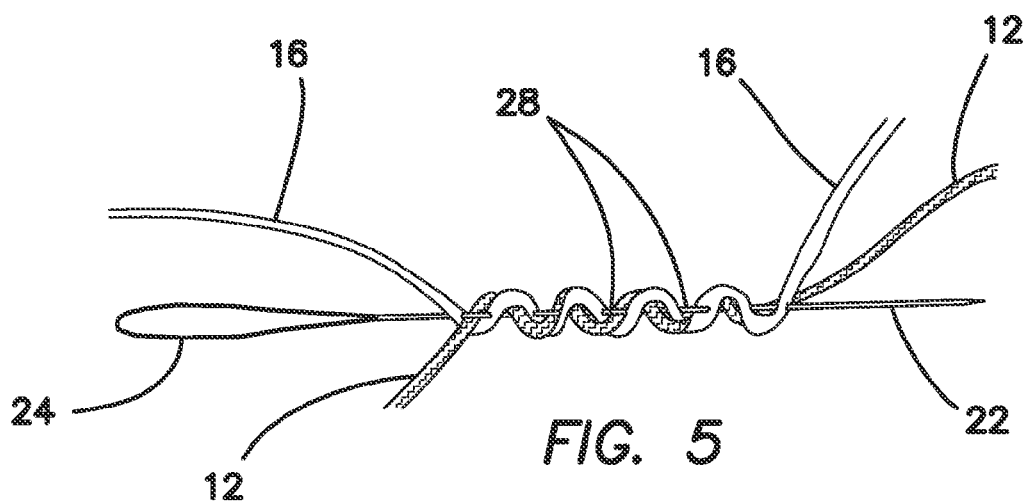
Figure 6:
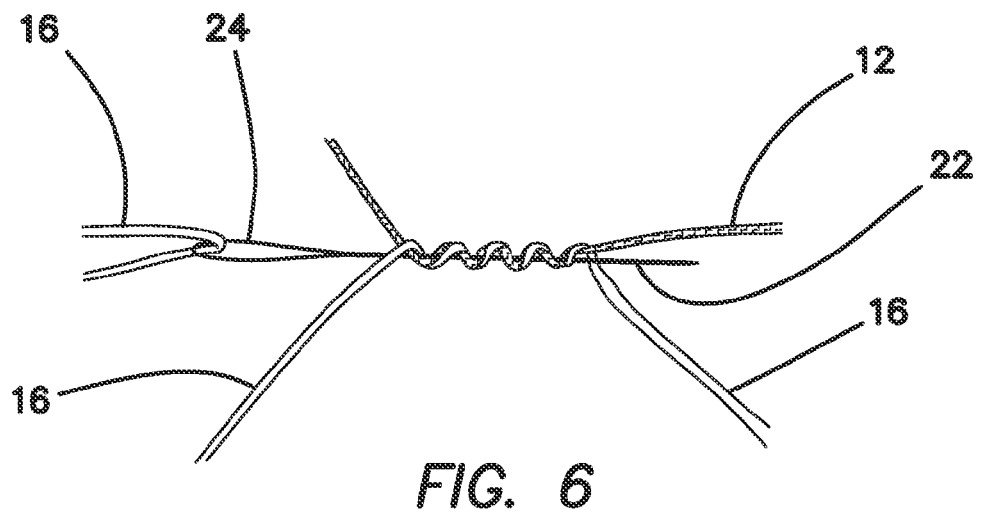
Figure 7:
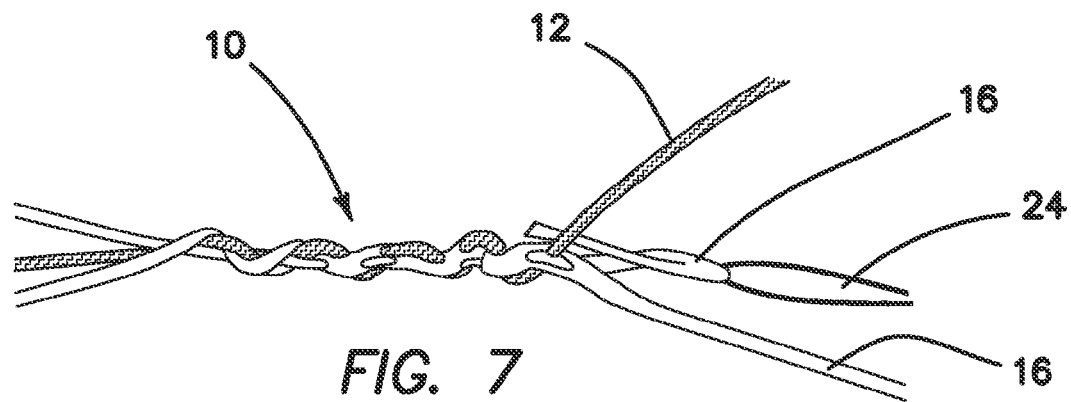

Referring to FIG. 5, one free end of the floating suture 12 is passed back and forth through, loops 28 formed between the suture 16 and the needle 22 in the previous step. As shown in FIGS. 6 and 7, one end of the anchor suture 16 is placed in the snare loop 24 and pulled back through the suture strand.

Figure 8:
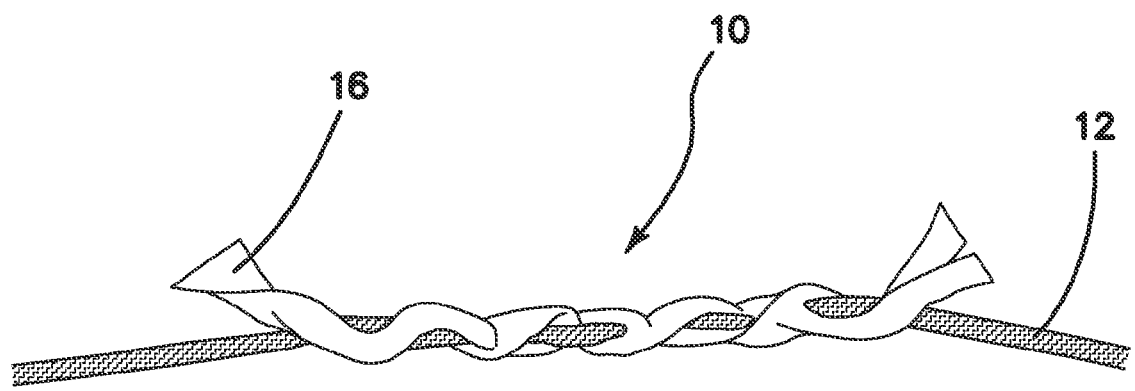

FIG. 8 illustrates a step wherein the floating suture 12 has been pulled tight, and the ends of the anchor suture have been cut off to complete the anchor construct 10.

Figure 9:
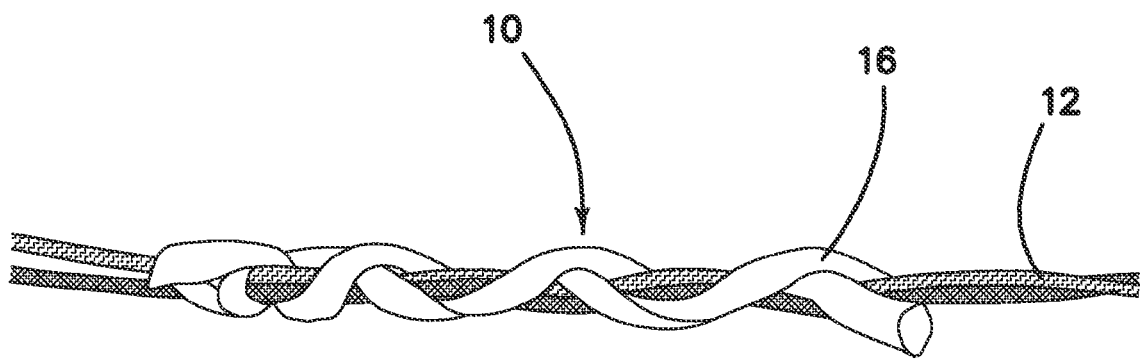
Figure 10:
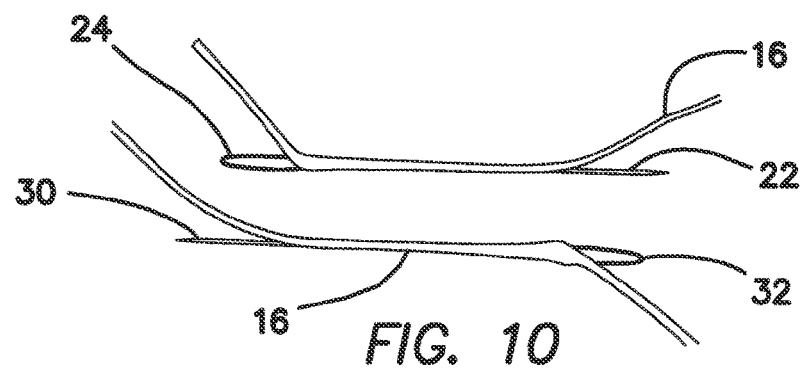
FIGS. 10-18 are views illustration the construction of a suture anchor according to a second embodiment of the invention.
Figure 11:
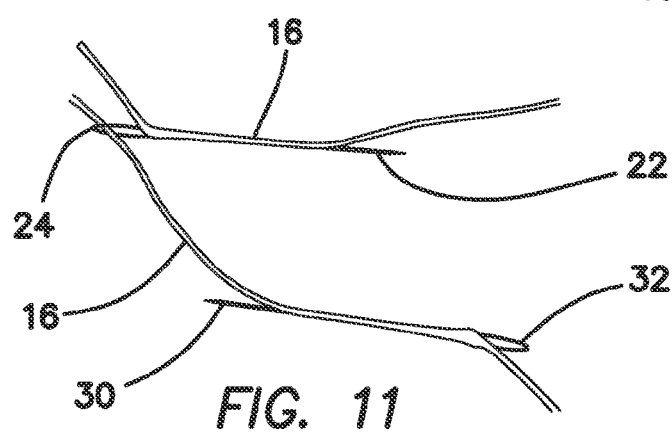
Figure 12:
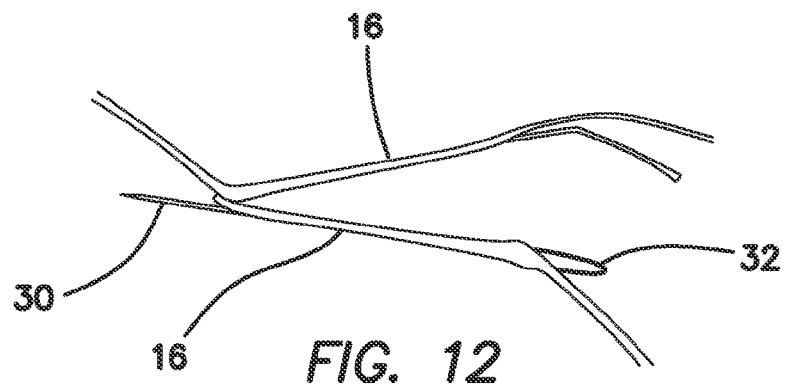
Figure 13:
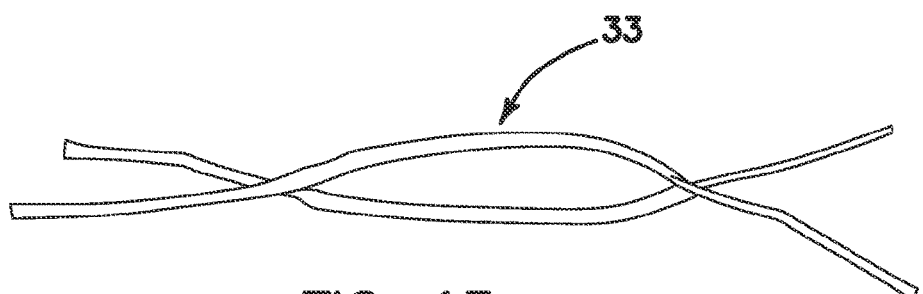

Now with reference to FIG. 9, a second embodiment of a suture anchor 10 constructed in accordance with the present invention is illustrated. This embodiment is a double-loaded anchor. This embodiment 10 is constructed as shown in FIGS. 10-18, FIG. 10 illustrates a first step in the method of constructing the double-loaded anchor 10 of FIG. 9, wherein a needle 22 with a snare loop 24 on the end is passed through the core of a size 2 piece of suture 16 (anchor suture). The step is repeated with a second needle 30 having a snare loop 32 being passed through a second piece of suture 16, as shown. In FIG. 11, the long end of second r anchor suture 16 is placed into the snare loop 24. The needle 22 is pulled to pull the suture end through the core of the second anchor suture 16. FIG. 12 illustrates the result of this step. Then, the long end of the first anchor suture 16 is placed in the snare loop 32 and pulled through the core of the second anchor suture 16. FIG. 13 illustrates the resulting anchor loop 33.

Figure 14:
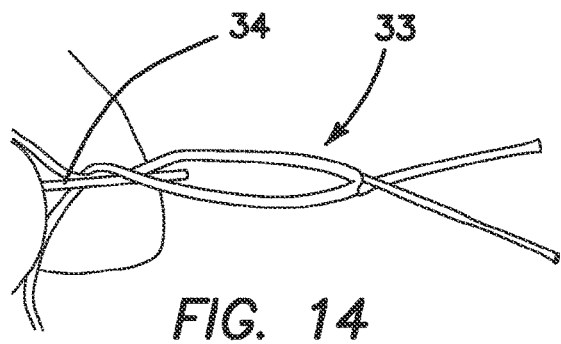
Figure 15:
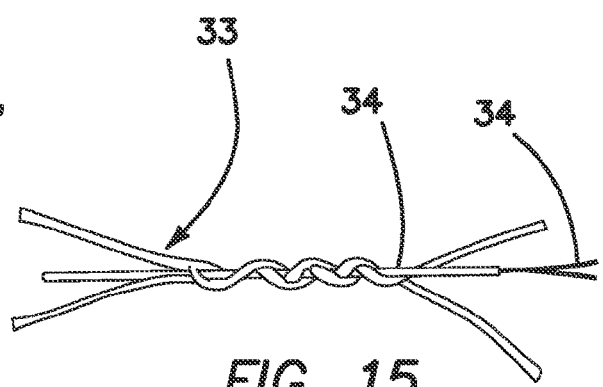
Figure 16:
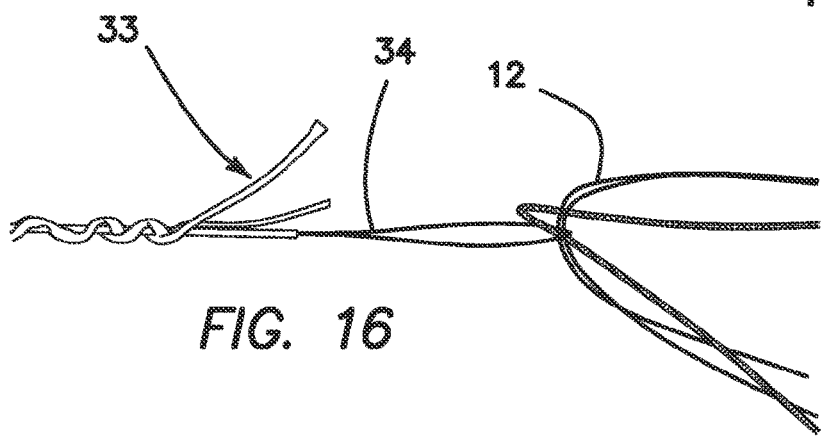

As shown in FIG. 14, to load the floating sutures 12, the loop 33 is placed over a suture snare 34. The anchor loop 33 is twisted in alternating directions around the suture snare 34, as shown in FIG. 15. Referring to FIG. 16, one free end of a floating suture 12 and two ends of the suture loop 33 are passed through the suture snare 34. The suture snare 34 is then pulled to pull the floating suture 12 and suture loop 33 through, the loops in the anchor.

Figure 17:
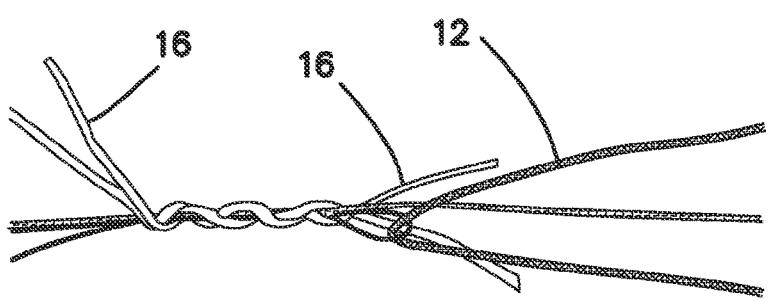

A second floating suture end is then passed through the suture loop 33, as shown in FIG. 17. The loop is pulled in the opposite direction to pull the second floating suture through the loops in the anchor.

Figure 18:
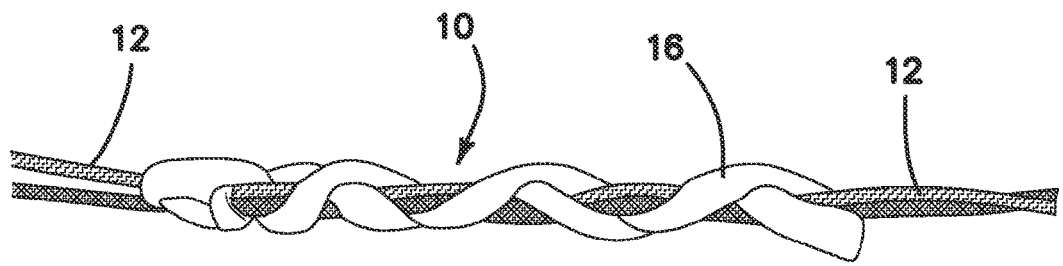

As represented in FIG. 18, the anchor suture ends are then trimmed to length, completing the assembly of the second embodiment of the suture anchor 10.

The two suture anchor embodiments 10 disclosed herein result in anchors that can be placed into a shallow, small diameter hole, and then when deployed by the inserter can be deployed into a large ball which is securely anchored in the bone tunnel.

Figure 19:
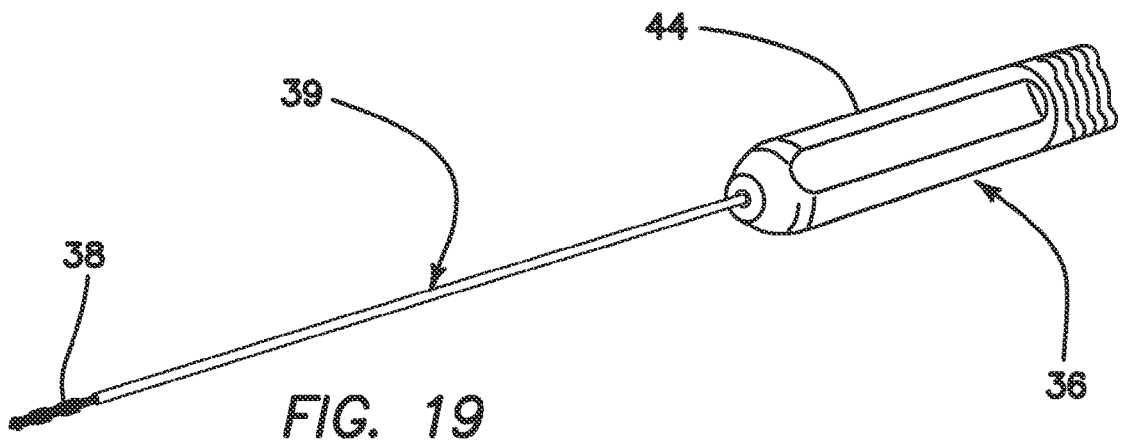
FIG. 19 is an isometric view of a suture anchor insertion system including an inserter constructed in accordance with the principles of the invention.
Figure 20:
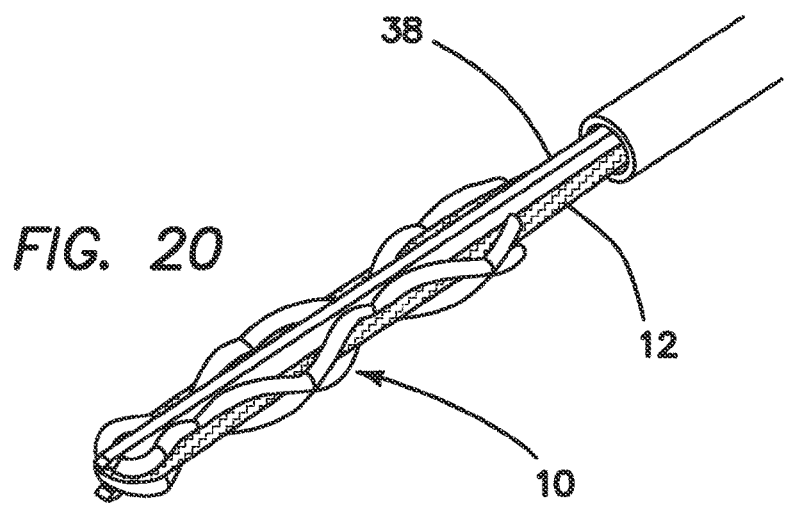
FIG. 20 is an isometric view of a distal end of the inserter of FIG. 19.

Now with reference to FIGS. 19-23, the inserter 36 of the present invention will be described. The inserter 36 has two primary functions. A first function is to deliver the anchor 10 into the bone tunnel, and a second function is to apply tension on the floating sutures 12 to deploy the anchor 10. One embodiment of the inserter 36 is illustrated in FIG. 19, comprising several components required to deploy the anchor. The following describes the anchor 10 loaded with one floating suture.

Figure 22:
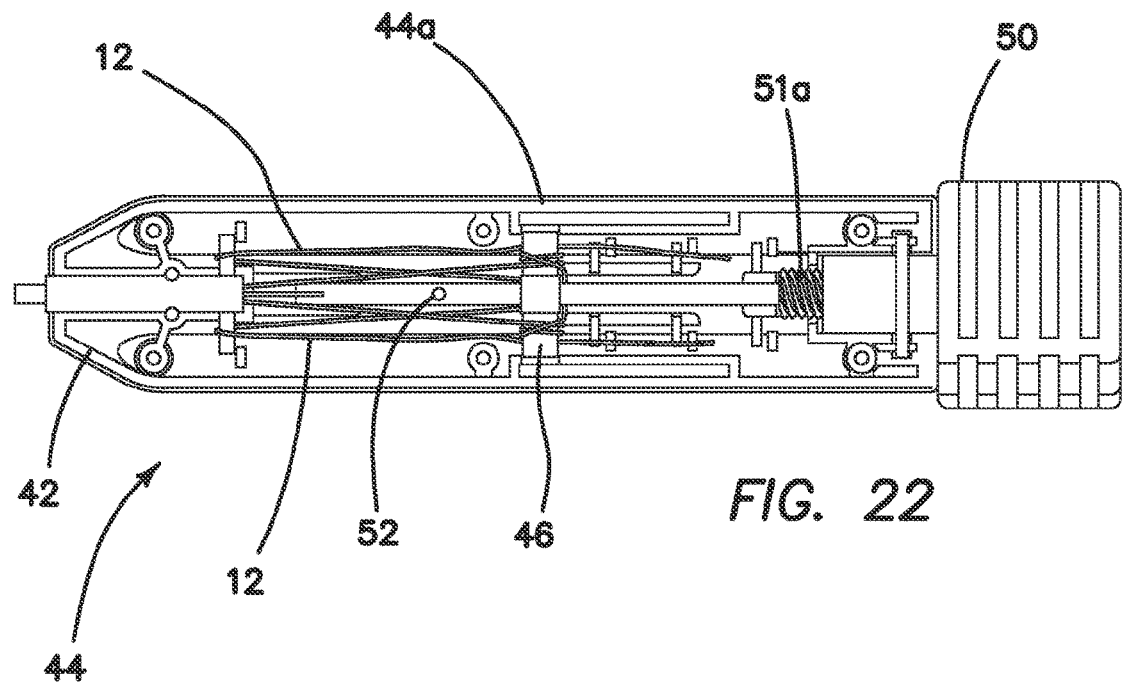
FIG. 22 is a schematic top view of the handle portion of tire inserter of FIGS. 19-20 and/or FIGS. 28-29, illustrating its inner mechanical features.

Inside the inserter 36, which comprises an inner shaft 38 housed within an outer shaft 39, as well as a handle 44 disposed at a proximal end of the outer shaft 39, the floating suture ends are wrapped around a crossbar 46 (FIG. 22). Wrapping the suture around the crossbar 46 provides friction in order to tension the floating suture 12 and deploy the anchor 10. After wrapping around the crossbar 46, the suture ends pass through a hole in the crossbar 46 and are compressed between a pinching pin 48 (FIG. 23) and an inner diameter of a hole in the crossbar 46. Compressing the sutures between the crossbar hole and the pinching pin 48 provides the small holding tension required to keep the sutures from slipping around the crossbar 46. The crossbar works like a capstan used in sailing. The tension to deploy the anchor ($T_{load}$) is counteracted by the sum of: 1) the friction of the suture wrapped around the crossbar, and 2) the friction of the suture compressed by the pinching pin 48 ($T_{hold}$). The relationship of these opposing forces is described by Eytelwein's formula:

$$T_{load}=T_{hold}e^{\phi\mu} \text{ where } \phi=\text{total angle swept around the Crossbar}$$

$\mu$=coefficient of friction between the suture and the crossbar materials

The design of the illustrated embodiment results in a range of $T_{hold}$ to achieve the desired deployment tension $T_{load}$ (60-150 N). The sutures are wrapped two times ($\phi=720°=2\pi$ radians) around the crossbar and the coefficient of friction is determined by the suture and crossbar materials. The size and length of the pinching pin 48, as well as the hole diameter in the crossbar 46 were chosen to achieve a specific range of holding tension, $T_{hold}$. The suture is pinched enough so that the minimum $T_{hold}$ is high enough to result, in a minimum $T_{load}$ of 60 N and the maximum $T_{hold}$ is low enough to result in a maximum $T_{load}$ of 150 N. The suture will begin to slip between the crossbar and the pinching pin when enough force is applied, keeping $T_{load}$ below the desired value.

Clearly, there are other methods of pinching the suture to provide the holding tension $T_{hold}$, such as spring clips, suture cleats, and the like. The suture ends are then wrapped inside the handle in such a way to allow them to unwrap and pay out of the inserter smoothly as it is removed after deployment.

After the inserter tip and anchor are inserted into the bone tunnel, the anchor is deployed by turning a knob 50 on the proximal end of the inserter 36. The knob 50 has an internal screw thread 51 that engages with an external thread 51*a* on the proximal end of the inner shaft 38. When the knob is rotated, the inner shaft is moved proximally. The inner shaft 38 also has a cross pin 52 that prevents it from rotating within the inserter 36 and pulls the crossbar 46 along with the inner shaft 38. For the first 9 mm of travel, the inner shaft 38 tip is pulling out of the bone tunnel and out from between the two sides of the folded-over anchor. This allows the anchor to move proximally dining deployment and provides space in the bone j-tunnel for the anchor to deploy. After the inner shaft 38 moves 9 mm, the cross pin 52 contacts the crossbar 46 and begins to pull it proximally in conjunction with the inner shaft. This travel of the crossbar pulls tension on the floating sutures 12 which enlarges the anchor and causes it to compress inside the bone tunnel. The inner shaft and crossbar travel for an additional 16 mm, which results in 60-150 N of tension ($T_{load}$) in the floating sutures.

Figure 23:
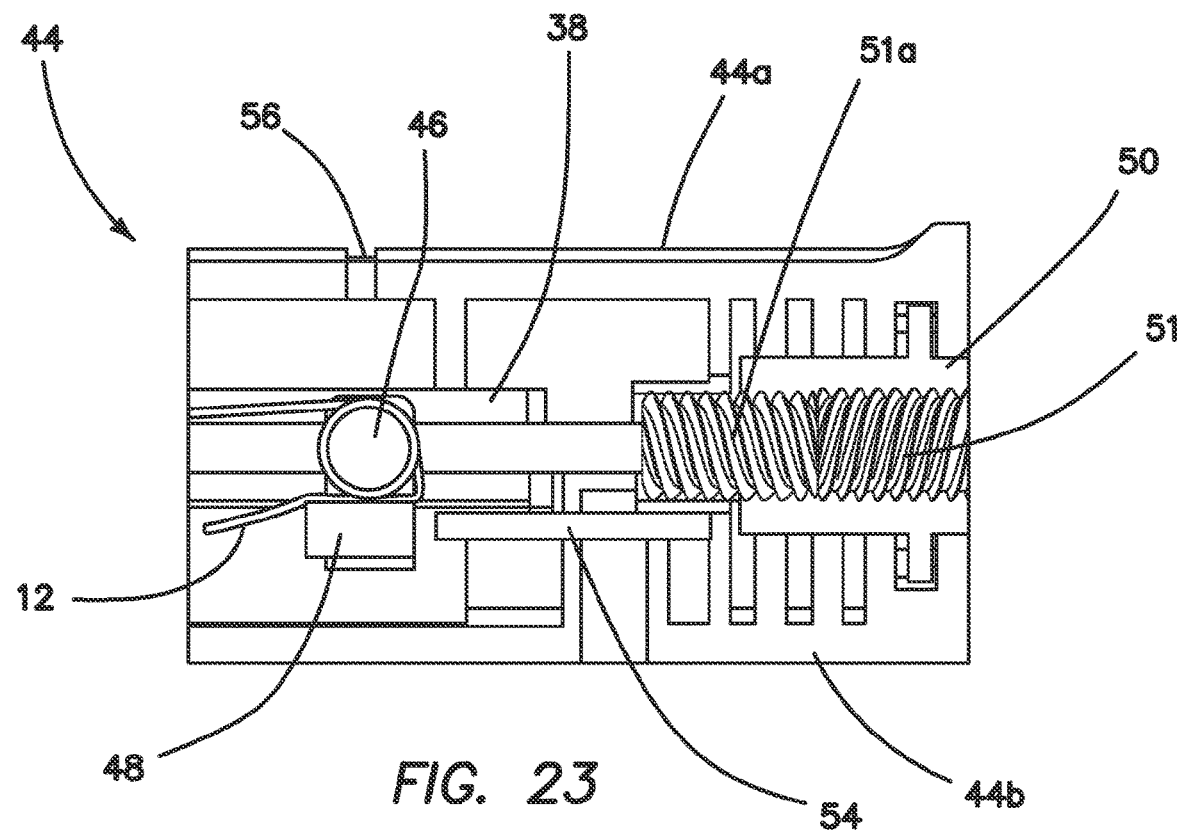
FIG. 23 is a schematic side view of the handle portion shown in FIGS. 21-22.
Figure 24:
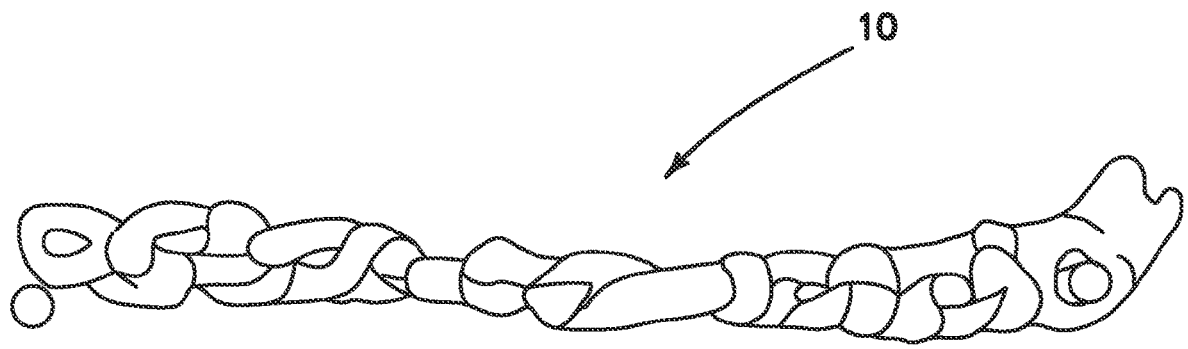
FIGS. 24-27 are views illustrating the construction of a suture anchor according to a third embodiment of the invention.

When the inner shaft reaches 20 mm of travel, the pinching pin 48 in the crossbar 46 contacts a smaller diameter fixed pin 54 in the handle 44 (FIG. 23). As it travels from 20 to 25 mm, the pinching pin 48 is pushed out of the crossbar to release the holding tension ($T_{hold}$) on the suture ends. When, the holding tension drops to zero, the tension on the floating sutures in the anchor ($T_{load}$) drops to zero and the sutures can slide and unwrap easily from the crossbar. At this point, the inserter is pulled proximally from the insertion site and the sutures unwrap and pay out of the inserter handle and deployment tube 42.

As noted above, the second anchor configuration. 10 is loaded with two floating sutures 12. In this case, two suture ends are routed up the deployment tube 42, with two limbs on either side of the inner shaft 38. One set of floating suture ends 12 are wrapped around the crossbar 46 and then routed through the handle 44 without capturing the ends with the pinching pin 48. The other set of floating sutures are wrapped around, the crossbar 46, captured by the pinching pin 48, and then, routed through the handle 44, as described previously. This allows one floating suture 12 to provide the tension required to deploy the anchor and pulls the other floating suture 12 along with the anchor 10 as it deploys. This helps to ensure proper deployment and ensures that both floating sutures 12 can slide easily within the anchor after if is deployed.

An additional feature is provided in the handle 44 to assist the practitioner. In the event that the floating suture 12 ends become tangled and caught in the handle during payout, suture access slots 56 (FIG. 23) are provided in the handle 44 to allow the practitioner to cut the suture ends with a scalpel. Tills leaves enough r length of floating suture 12 for the practitioner to complete the procedure. Reviewing FIG. 23, which is a depiction of the handle portion 44 of the inserter 36, the handle top 44a and handle bottom 44b are illustrated for clarity.

Another consideration for the design of the inserter shaft 39 is the ability to pass through a curved drill guide. In order to reach some locations (i.e. low on the glenoid rim), and to provide an angle as close to perpendicular to the surface as possible, a drill guide 58 (FIG. 21) with an approximately 25 degree curve is used. The inserter shaft 39 is flexible enough to pass through this curved guide.

Figure 21:
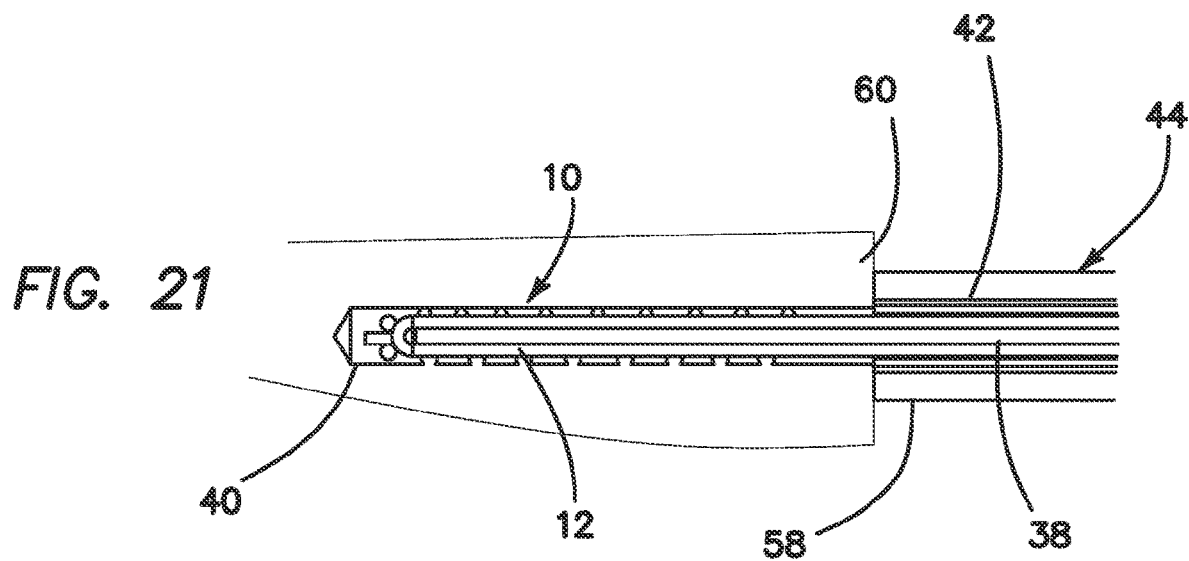
FIG. 21 is a schematic cross-sectional view showing the use of the inserter system of FIGS. 19-20 and/or FIGS. 28-29 to insert a suture anchor into a bone tunnel.

The drill guide 58 is designed to work in conjunction with the inserter 36 to deploy the anchor 10. The large surface area at the distal tip of the drill guide 58 lowers the pressure exerted on the hone surface 60 during anchor deployment (FIG. 21). There are, in certain embodiments, two sizes of drill guides for the two anchor configurations, though, of course, the inventive system contemplates the usage of more than two different anchor configurations with a corresponding number of suitable drill guides. The single-loaded anchor drill guide, in one illustrative embodiment, has a tip surface area of 8.65 mm$^2$, compared to approximately 4.25 mm$^2$ for a typical drill guide tip, an approximate 2:1 ratio. This reduces the pressure on the bone by about one half for the same applied force and greatly reduces the risk of the tip cutting into the bone during anchor deployment or practitioner over-malleting. It also provides an opposing force over a large surface area on the bone surface, above the deploying anchor, to prevent the anchor from pulling out of the bone during tension.

Figure 25:
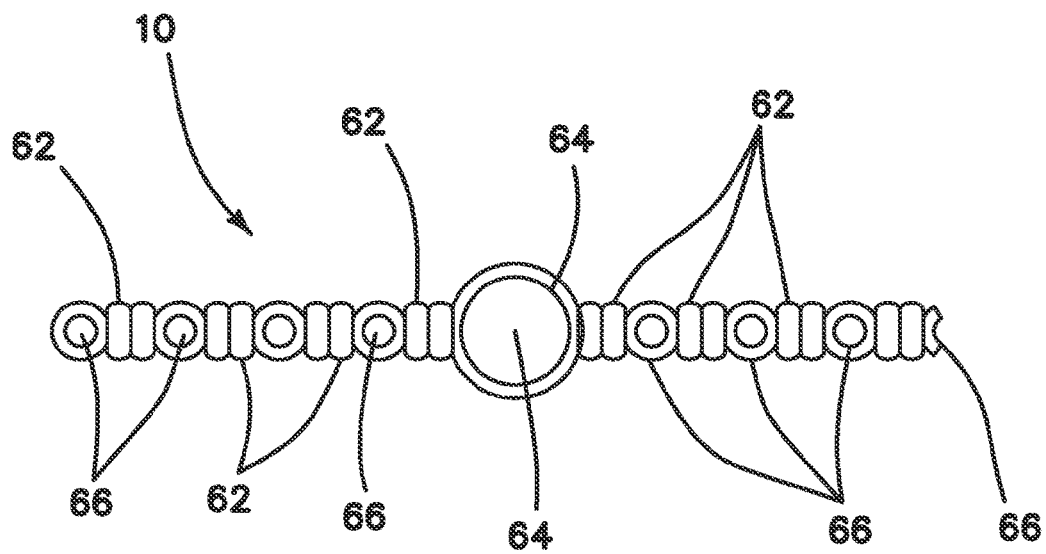
Figure 26:
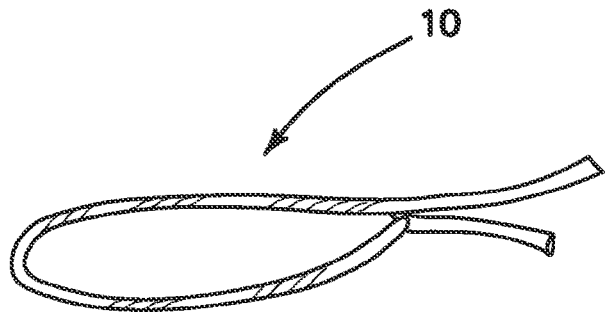
Figure 27:
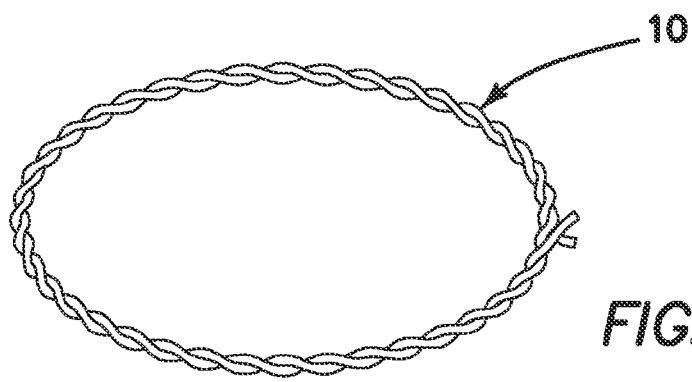

Another alternative suture anchor embodiment 10 is illustrated in FIGS. 24-27. This anchor is constructed by wrapping anchor suture around a pin and tying two alternative half-hitches 62 (FIG. 25). The two limbs are then wrapped around another pin, and more half-hitches 62 are tied. The center loop 64 is wrapped around a larger pin to allow for easier loading onto the inserter inner shaft 38. The floating suture or sutures are then passed through the loops 66 (created by the pins) to complete the construct.

This anchor is constructed by forming a double loop of suture, then wrapping one of the free ends around the loop approximately twenty times. The loop is then tightened around two posts a distance apart by pulling both free ends. This creates a loop, similar to the anchor loop of the previous double-loaded anchor embodiment 10 of FIGS. 10-18. The remaining construction steps are the same as previously described—the anchor is wrapped around a snare with alternating twists and a floating suture is pulled through the openings to complete the construct.

Figure 28:
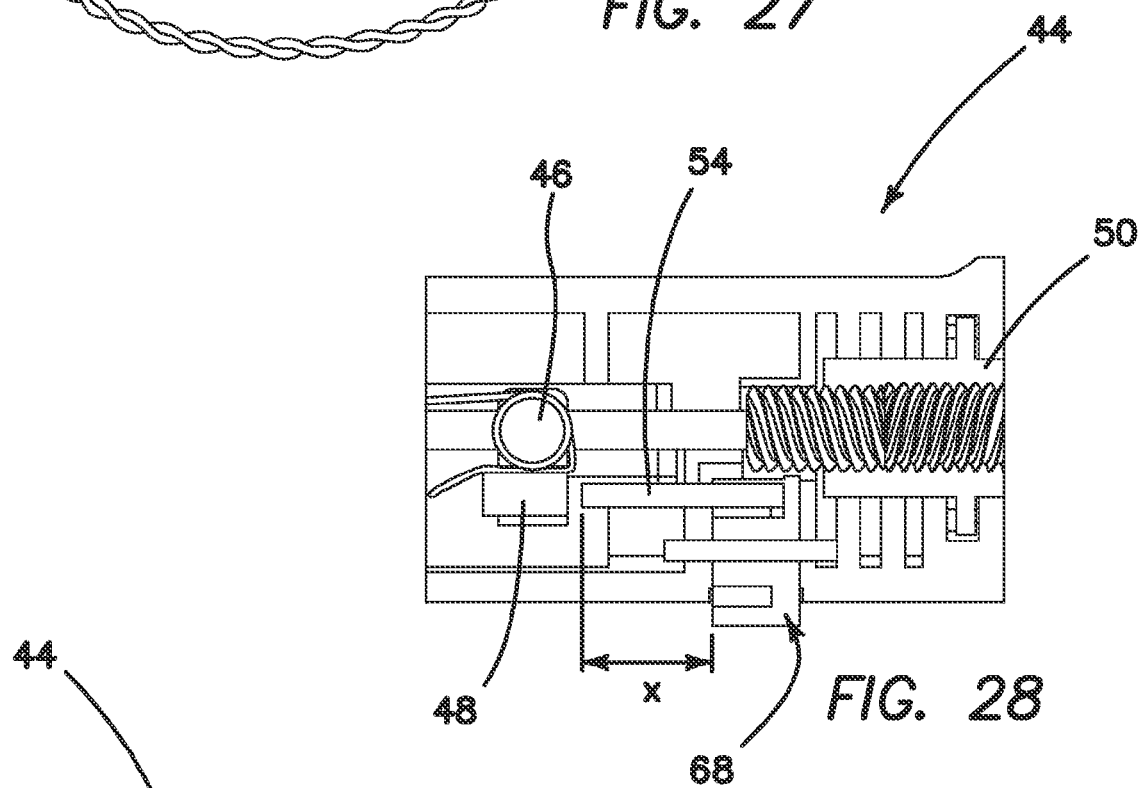
FIGS. 28 and 29 are schematic views illustrating an alternative embodiment of the inserter handle of the present invention, which is similar in all respects to the embodiment illustrated in FIGS. 22-23 except for the addition of an ability to adjust tension control of the inserter system.
Figure 29:
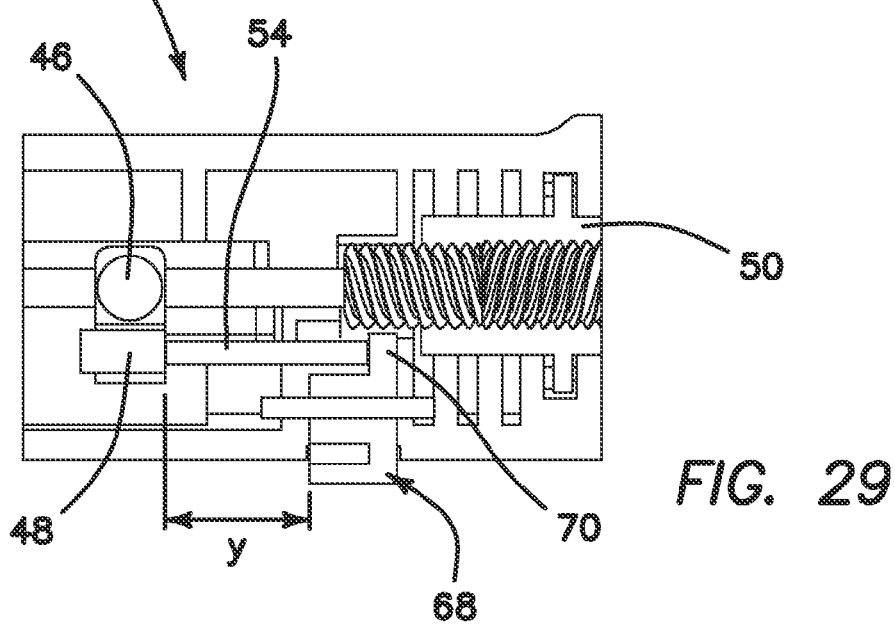

In the foregoing described embodiments of the inserter 36, the crossbar 46 travels a fixed distance before the sutures are released, resulting in a predetermined tension range to deploy the anchor 10. If desired, however, this distance—and therefore, the deployment tension—can be adjusted by the practitioner. For example, the practitioner may be concerned about deploying in very soft or poor bone quality, and may want to deploy the anchor with a lower tension. The lower pullout force can be compensated for by implanting more anchors or further restricting the patient's post-operative activity. An embodiment of this modified design is illustrated in FIGS. 28 and 29. In this embodiment, adjustable deployment tension requires an adjustable tension control knob or switch 68 that the user can adjust as desired. In FIG. 28, the adjustable tension control 68 serves as a backstop and determines the position of the fixed pin 54. In this first position, the fixed pin 54 is in a proximal position a distance x from the control 68, which in one illustrative embodiment is approximately 12 mm, and contacts the pinching pin 48 when the crossbar 46 reaches 20 mm of travel. The pinching pin 48, and thus the deployment tension ($T_{load}$) is released when the crossbar travels 25 mm, in the illustrated example. This is the high deployment tension position (the same as in the fixed embodiment described above).

However, when the adjustable tension control 68 is actuated to its second position, as shown in FIG. 29, a ramp 70 pushes the fixed pin distally, so that the fixed pin is in a distal position a distance y from the tension adjustment control 68. In the same illustrative embodiment, this distance y is approximately 14 mm. In this position, the pinching pin 48 contacts the fixed pin when the crossbar 46 reaches 18 mm of travel. The pinching pin, and thus, the deployment tension ($T_{load}$), is released when the crossbar 46 travels 23 mm. This reduced travel results in a lower maximum tension ($T_{load}$) applied to the floating sutures to deploy the anchor.

The tension adjustment control 68 may have two positions, as illustrated, comprising a "hard bone" position and a "soft bone" position, or if may alternatively be infinitely adjustable. The same function may be achieved with a slider or any other actuator which changes the position of the fixed pin with respect to the crossbar and the pinching pin.

In the foregoing embodiments, the maximum tension applied by the inserter is limited by the fit of the fixed pin inside the crossbar-. The floating sutures are pinched between these two components. When the tension becomes too high, the sutures will slip, placing a limit on the holding tension $T_{hold}$, and thus, on the deployment tension $T_{load}$. If a more precise maximum deployment force were desired, the deployment tension applied to the floating sutures could be limited by utilizing a compression spring between the cross pin and the crossbar. In such a design, when the tension in the floating sutures exceeds the force exerted by the spring at the given length, proximal movement of the cross pin would simply compress the spring and not continue to move the crossbar proximally. Because the crossbar would not move, the only additional tension applied to the floating sutures would be through the spring. By choosing the proper spring parameters (length, spring rate) and distances between the cross pin and crossbar, a maximum force may be applied to the crossbar by the cross pin (through the spring), resulting in a maximum tension applied to the suture to deploy the anchor.

In the described inserter embodiments, the suture is wrapped mound a round crossbar in order to pull considerable tension on the floating sutures. There are other methods, however, which may be used to secure the floating sutures, including spring clips, suture cleats, and the like. A pinching pin is provided to secure the suture ends. This pin is released automatically when the inner shall moves the designed distance. This pin may be replaced by a simple suture cleat on the crossbar and rely on the user to release the holding tension manually. This would require the suture ends to be accessible outside the handle.

Accordingly, although exemplary embodiments of the invention has been shown and described, it is to be understood that all the terms used herein are descriptive rather than limiting, and that many changes, modifications, and substitutions may be made by one having ordinary skill in the art without departing from, the spirit and scope of the invention.

What is claimed is:

1. A method of manufacturing a bone anchor device, comprising:
   folding a first suture back and forth upon itself to create a folded section of the first suture in which a first plurality of folds face in a first direction and a second plurality of folds face in a second direction opposite the first direction, the folded section located along the first suture between a first free end of the first suture and a second free end of the first suture;
   moving an elongated snare device along a path through the folded section so that the first plurality of folds are located on a first side of the elongated snare device and the second plurality of folds are located on a second side of the elongated snare device opposite the first side, wherein said passing forms a separate loop between the elongated snare device and each fold in the first plurality of folds and a separate loop between the elongated snare device and each fold in the second plurality of folds;
   passing a first free end of a second suture through each of said separate loops; and
   pulling the first free end of the first suture back along the path through the folded section with the elongated snare device.

2. The method of claim 1, wherein the folded section is created in an assembly fixture.

3. The method of claim 2, wherein the first suture is folded back and forth upon itself around pins in the assembly fixture.

4. The method of claim 1, wherein the elongated snare device comprises a needle.

5. The method of claim 1, wherein the elongated snare device comprises a snare loop.

6. The method of claim 1, wherein the first suture is a size 2 suture.

7. The method of claim 1 further comprising removing a portion of the first free end of the first suture after said pulling step.

8. The method of claim 7 further comprising removing a portion of the second free end of the first suture after said pulling step.

9. The method of claim 1, wherein said moving of the elongated snare device along said path includes initially passing the elongated snare device laterally through the first suture at a first location along the first suture that is proximate the second free end of the first suture so that said pulling of the first free end of the first suture back along the path with the elongated snare device pulls the first free end of the first suture laterally back through the first suture at the first location.

10. The method of claim 1, wherein said pulling of the first free end of the first suture back along the path through the folded section causes the first free end of the first suture to be pulled laterally through the first suture multiple times.

11. The method of claim 1, wherein said pulling of the first free end of the first suture back along the path through the folded section causes the first free end of the first suture to exit the first suture a final time proximate the second free end of the first suture.

12. The method of claim 1, wherein the first suture provides an anchoring element of the bone anchor device, and wherein the second suture provides a tensioning element of the bone anchor device.

13. The method of claim 12 further comprising engaging the first suture with a leading end of a delivery shaft and having the first free end of the second suture and a second free end of the second suture extend back along the delivery shaft away from the first suture.

14. The method of claim 13, wherein the anchoring element provided by the first suture is loaded onto the leading of the delivery shaft in a folded delivery configuration.

15. A bone anchor device manufactured in accordance with claim 1.

16. The bone anchor device of claim 15, wherein the first suture provides an anchoring element of the bone anchor device, and wherein the second suture provides a tensioning element of the bone anchor device.

17. The bone anchor device of claim 16, wherein the first suture is loaded onto a leading end of a delivery shaft, and wherein the first free end of the second suture and a second free end of the second suture extend back along the delivery shaft away from the first suture.

18. The bone anchor device of claim 17, wherein the anchoring element provided by the first suture is loaded onto the leading of the delivery shaft in a folded delivery configuration.

* * * * *